United States Patent [19]

Gray et al.

[11] Patent Number: 5,056,365
[45] Date of Patent: Oct. 15, 1991

[54] COLLISION SENSOR

[75] Inventors: Floyd L. Gray, Muskego; Duane A. Filtz, Brookfield; Jonathan C. Boomgarden, Waukesha; Timothy F. Hamers, Windlake, all of Wis.

[73] Assignee: General Electric Company, Milwaukee, Wis.

[21] Appl. No.: 531,222

[22] Filed: May 31, 1990

[51] Int. Cl.$^5$ .............................................. H05G 1/02
[52] U.S. Cl. .................................... 73/432.1; 378/117
[58] Field of Search .................... 378/117, 197; 73/11, 73/12, 865.7, 432.1

[56] References Cited

U.S. PATENT DOCUMENTS

| 4,733,408 | 3/1988 | Beikuefner et. al. | 378/117 |
| 4,969,170 | 11/1990 | Kikuchi et al. | 378/117 X |
| 4,987,583 | 1/1991 | Travanty et al. | 378/197 X |

FOREIGN PATENT DOCUMENTS 3343924  6/1985  Fed. Rep. of Germany ...... 378/117

OTHER PUBLICATIONS

Applicant's Exhibit No. 1, cross-sectional view of collision sensor, admitted prior art.
Applicant's Exhibit No. 2, GE Medical Systems, Advantx Card POS SP/BP Fluoro Schematics, Rev. B, Direction 19310, p. 24-2, admitted prior art.

Primary Examiner—Hezron E. Williams
Assistant Examiner—Joseph W. Roskos
Attorney, Agent, or Firm—Quarles & Brady

[57] ABSTRACT

A collision sensor specially adapted for a power driven x-ray imaging apparatus includes a face collision sensor and an edge collision sensor. The face collision sensor has two annular plates which are biased apart longitudinally by three flat springs which are equiangularly spaced apart around the perimeter of the plates. Three equiangularly spaced cables hold the plates in parallel planes with the springs prestressed and collapse to allow the plates to be compressed together. Two sets of three switches each reside at equal angular intervals between the plates, with at least one of the switches of the first set being actuated when any point across the face of the sensor has been moved a predetermined longitudinal distance. At least one of the switches of the second set is actuated when the point on the face of the sensor has been moved a further predetermined longitudinal distance. An edge collision sensor includes a closed air bladder which surrounds the face collision sensor and in which a vacuum is drawn. A collision occurring around the edge of the face collision sensor causes an increase in the pressure of the bladder. A first pressure sensor is actuated if the pressure increase exceeds a first predetermined amount. A second pressure sensor is actuated if an additional predetermined increase in pressure occurs.

21 Claims, 4 Drawing Sheets

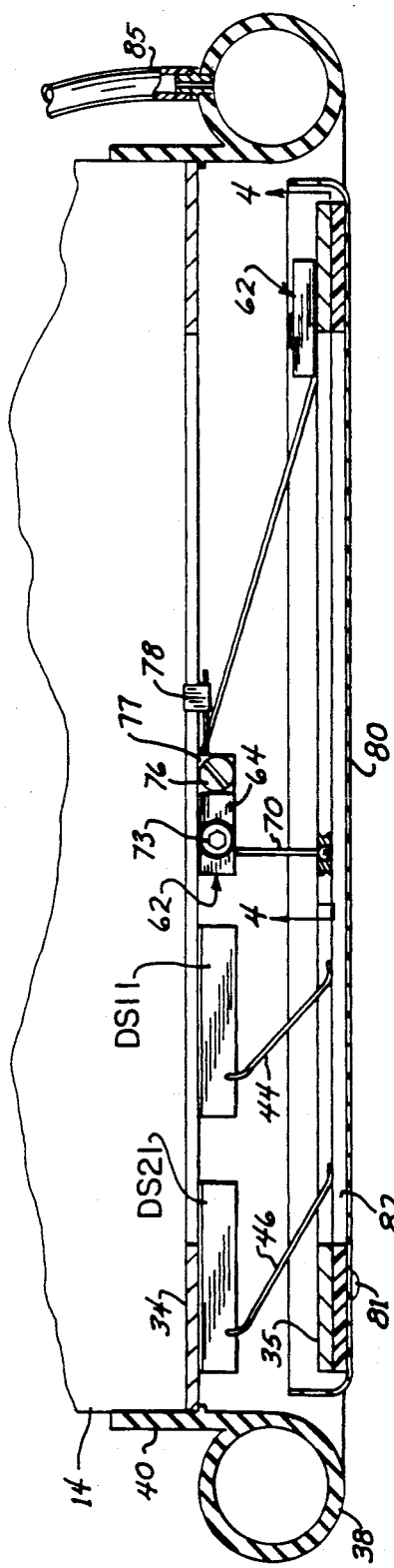
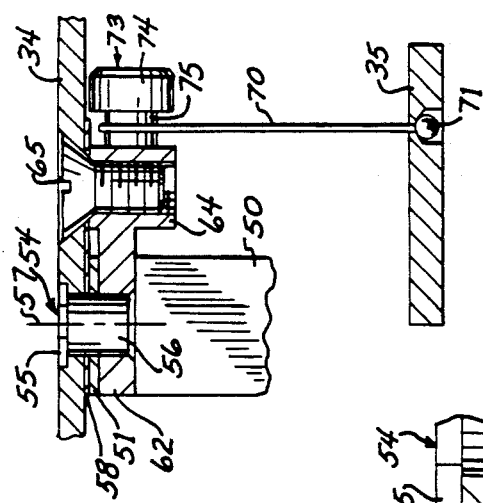
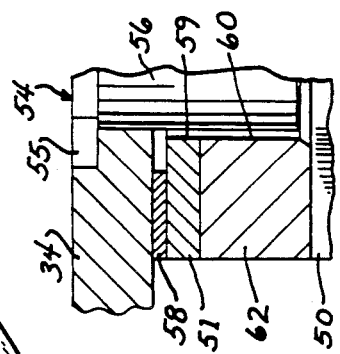
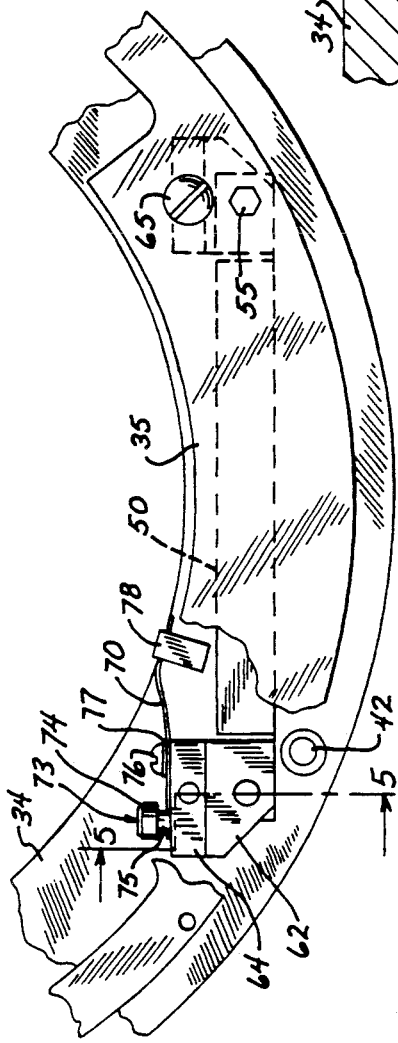

COLLISION SENSOR

FIELD OF THE INVENTION

The field of the invention is sensors for mounting on movable machines or components thereof for detecting when the machine has collided with an object or person, and particularly for such sensors for medical diagnostic equipment such as x-ray machines.

DISCUSSION OF THE PRIOR ART

Medical diagnostic x-ray equipment has typically included an x-ray transmitter and an image receiver spaced apart from the transmitter along a longitudinal axis. The person or object to be x-rayed is placed between the transmitter and the receiver. The transmitter and receiver is then positioned relative to the body to produce an image in the desired plane.

Such machines have usually been constructed so as to be counter-weighted and manually positionable. However, these types of machines are now being power driven for greater utility in specific applications, such as cardiac imaging or profiling of a blood vessel. Such a power driven x-ray apparatus is disclosed in commonly owned U.S. application Ser. No. 07/333,291, filed Apr. 4, 1989, entitled "X-Ray Positioner For Multi-Access Profiling".

It is important to move the image receiver as closely as possible to the patient to produce a clear image. The receiver has a relatively large face area through which x-rays are received. Any part of this area, or any part of its periphery, may come in contact with the patient and therefore the receiver must be sensitive over its entire facial area to collisions with the patient, which may occur in any direction that the receiver is moved. This type of x-ray diagnostic equipment also moves relatively rapidly so quick actuation in response to relatively low forces, which may be applied at any point across the facial area of the receiver and in any direction, is necessary.

In power driven machines, it is important to provide a fail-safe mechanism which will sense when the machine has collided with an object or person. Upon sensing a collision, the mechanism can sense the collision to stop the machine before any damage is done.

SUMMARY OF THE INVENTION

The invention provides a collision sensor having a base plate defining a base plane and a longitudinal axis. A support plate is spaced apart from the base plate along the longitudinal axis, defines a support plane and is biased away from the base plate along the longitudinal axis. Collapsible, non-distensible extension limiting means extend between the base plate and the support plate in a direction generally parallel to the longitudinal axis for positioning the support plane parallel to the base plane when the limiting means are fully extended, and means are positioned between the base and support plates for sensing the proximity of the support plate to the base plate. This construction provides an inexpensive collision sensor which can be used to reliably signal collisions occurring anywhere across a relatively large area and having a relatively small axial force component with a quick response time.

In a preferred form, the collision sensor is specially adapted for mounting on a power driven x-ray receiver. The base and support plates are ring shaped to define a radiation transmission path therethrough along the longitudinal axis, and a face plate made of a low x-ray attenuation material covers the support plate. Thereby, a collision occurring anywhere across the face of the sensor can actuate the sensor, without the sensor interfering with the transmission of x-rays to the image receiver.

In another aspect, the extension limiting means includes three rope-like lines connecting the base plate to the support plate at spaced apart angular locations about the longitudinal axis. Each line is secured on the base plate, extends to and wraps partially around a block on the base plate, and from there extends and is secured to the support plate. When the base and support plates are compressed together, each line collapses in a controlled, generally circumferential direction, so as not to interfere with the x-ray transmission or the operation of any of the other components of the sensor.

In an especially useful form, the biasing means is one or more flat springs which extend between the base plate and the support plate. Preferably, three flat springs extend between the base plate and the support plate at locations which are equally spaced apart angularly about the longitudinal axis. Each of the springs angles from the base plate to the support plate in generally the same circumferential direction, i.e., clockwise or counterclockwise, so as to allow free operation of the springs as the base and support plates are compressed together and to return the support plate to a parked position with minimum hysteresis. In this construction, the sensing means can include at least one mechanically actuated switch having a rotary actuator arm angling from the base plate to the support plate in generally the same circumferential direction that the springs extend from the base plate to the support plate. In this construction, the rotation imparted to the support plate as a result of compressing the support plate toward the base plate tends to actuate the switch.

Each flat spring preferably has one end adjacent to the base plate and an opposite end adjacent to the support plate. Means should be provided for securing each of the ends to the adjacent plate to allow the spring to rotate slightly about an axis parallel to the longitudinal axis when the base and support plates are compressed together. In the embodiment disclosed, the securing means provides a loosely pinned connection between each spring end and the adjacent plate. This also helps reduce hysteresis in the springs.

In the embodiment disclosed, two levels of switching are provided to assure fail safe operation. A first set of at least three switches is fixed to the base plate and is angularly spaced approximately 120° apart about the longitudinal axis. Each switch has an actuator arm which extends toward the support plane for actuation when the longitudinal spacing between the support plane and the base plane at the position of the switch has been reduced by a first predetermined travel. A second set of at least three switches is also fixed to the base plate and angularly spaced approximately 120° apart about the longitudinal axis. The switches of the second set each have an actuator arm which extends toward the support plane for actuation when the longitudinal spacing between the support plane and the base plane at the position of the switch has been reduced by a second predetermined travel which is greater than the first predetermined travel. If the collision sensor is mounted to a power driven member of a machine, the difference between the first predetermined travel and the second predetermined travel should be chosen to be greater than the over travel which the member goes through after at least one of the first set of switches is actuated. Actuation of only one or more of the first level switches can therefore be used to signal an accidental collision so as to stop the machine, and actuation of one or more of the second level switches can be used to not only stop the machine but also signal a machine malfunction. In an especially preferred form, the collision sensor also includes a pressure sensitive bladder which surrounds the support plate and produces a signal in response to a collision having a radial force component, so as to protect the entire periphery of the axial collision sensor.

BRIEF DESCRIPTION OF THE DRAWINGS

FIG. 2 is a cross-sectional view taken along the line 2—2 of FIG. 1, and more specifically along the line 2—2 of FIG. 3, showing a collision sensor of the invention mounted to the x-ray imaging apparatus of FIG. 1;

FIG. 4 is a fragmentary bottom plan view of a portion of the face collision sensor;

FIG. 5 is a cross-sectional view taken along the line 5—5 of FIG. 4;

FIG. 6 is a detail view of a portion of FIG. 5;

DETAILED DESCRIPTION OF THE PREFERRED EMBODIMENT

Figure 1:
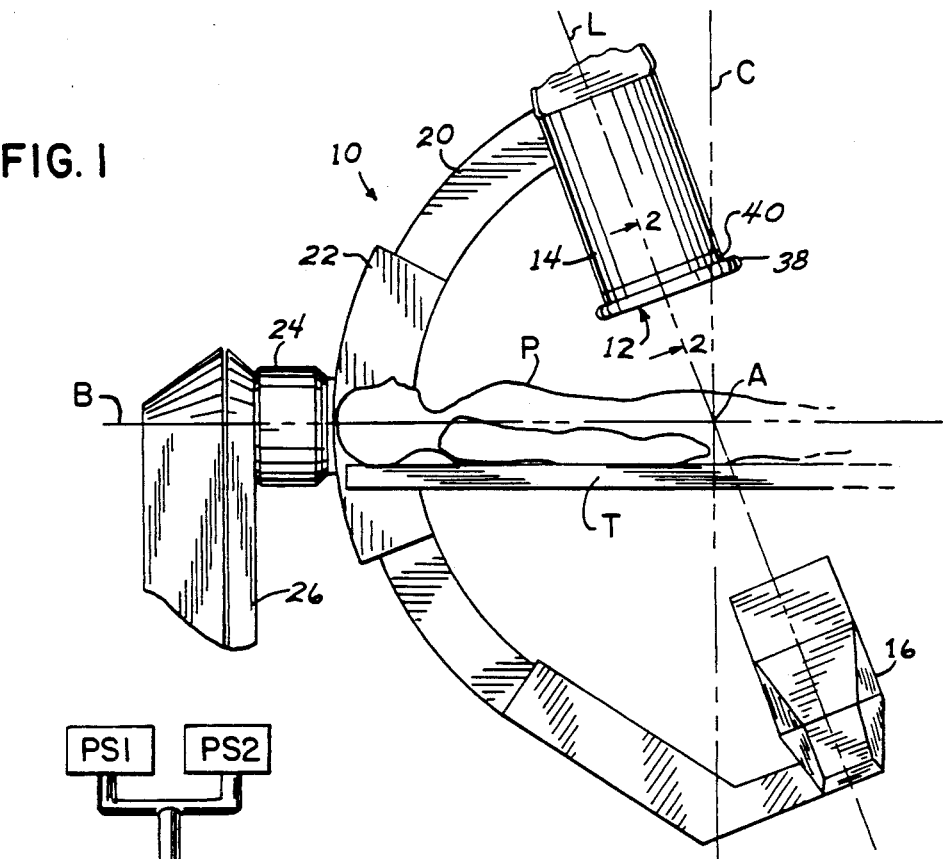
FIG. 1 is a perspective view of a medical diagnostic x-ray imaging machine fitted with a collision sensor of the invention.

Referring to FIG. 1, a medical diagnostic x-ray imaging apparatus 10 is illustrated which incorporates a collision sensor 12 of the invention. The imaging apparatus 10 has an image receiver 14 and an x-ray transmitter 16 spaced apart from the image receiver 14 along a longitudinal axis L. The image receiver 14 and the transmitter 16 are mounted at opposed ends of an arcuate arm 20 which rides in trackway 22. The arm 20 can be driven in trackway 22 to rotate the image receiver 14 and transmitter 16 in the plane of arm 20 about axis A, which as shown in FIG. 1 extends into the plane of the paper.

The image receiver 14 and x-ray transmitter 16 may also be rotated about axis B, which extends through bearing 24 which connects trackway 22 to upstanding leg 26. Leg 26, and therefore image receiver 14 and x-ray transmitter 16, may further be rotatable about a vertical axis C. All of the rotary motions about these three rotational axes may be power driven. An x-ray imaging machine of this configuration is disclosed in commonly owned U.S. application Ser. No. 7/333,291 filed Apr. 4, 1989, which is hereby incorporated by reference herein.

In operation, a patient P is supported on a table T between the image receiver 14 and the transmitter 16 and the x-ray imaging apparatus is driven to rotate the longitudinal axis L so as to produce an image in any desired plane through the patient. Since the receiver 14 is power driven in proximity to the patient and to other apparatus, the collision sensor 12 of the invention is provided to automatically stop movement of the receiver 14 in case a collision with the collision sensor 12 is detected. As can be seen in FIG. 1, the collision sensor 12 is located at the inner end of the image receiver 14, which would be the most likely area of the machine 10 to first contact a patient.

FIG. 2 shows a cross-sectional view of the collision sensor 12. A collision may occur by contact at any point across the face of the image receiver 14, or a collision may occur with the lower edge of the image receiver 14. Accordingly, a face collision sensor 30 is provided to sense collisions across the face of the image receiver 14 and a separate edge collision sensor 32 is provided to sense collisions which may occur around the lower edge of the image receiver 14. Because the face collision sensor 30 is primarily for sensing collisions having an axial force component it may also be referred to as an axial collision sensor, although it should be understood that the collision may also have a radial force component due to friction with the sensor 30 or contact with an edge surface of the sensor 30. Likewise, the edge collision sensor 32 is primarily for sensing collisions having a radial force component and therefore may be referred to as a radial collision sensor, although it would also operate to sense collisions having an axial component.

The face collision sensor 30 and the edge collision sensor 32 are separate from one another, the face collision sensor 30 being a generally disk shaped arrangement of two longitudinally spaced apart plates 34 and 35. The edge collision sensor 32 has a toroidally shaped air bladder 38 and a flange 40 for mounting the the air bladder 38 to the image receiver 14.

The face collision sensor 30 is nested within the bore defined by the edge collision sensor 32 and is mounted on the face of the image receiver 14 which is normally adjacent to a patient. The face collision sensor 30 shown in FIG. 2 is shown in a normal, unactuated, parked position in which the planes defined by the plates 34 and 35 are generally parallel and spaced approximately 1.25 inches apart. In this position, the face collision sensor 30 may extend slightly beyond the bottom face of the edge collision sensor 32, but preferably not so far that the edge of the sensor 30 would be susceptible to being engaged in case of a sideways collision.

Figure 3:
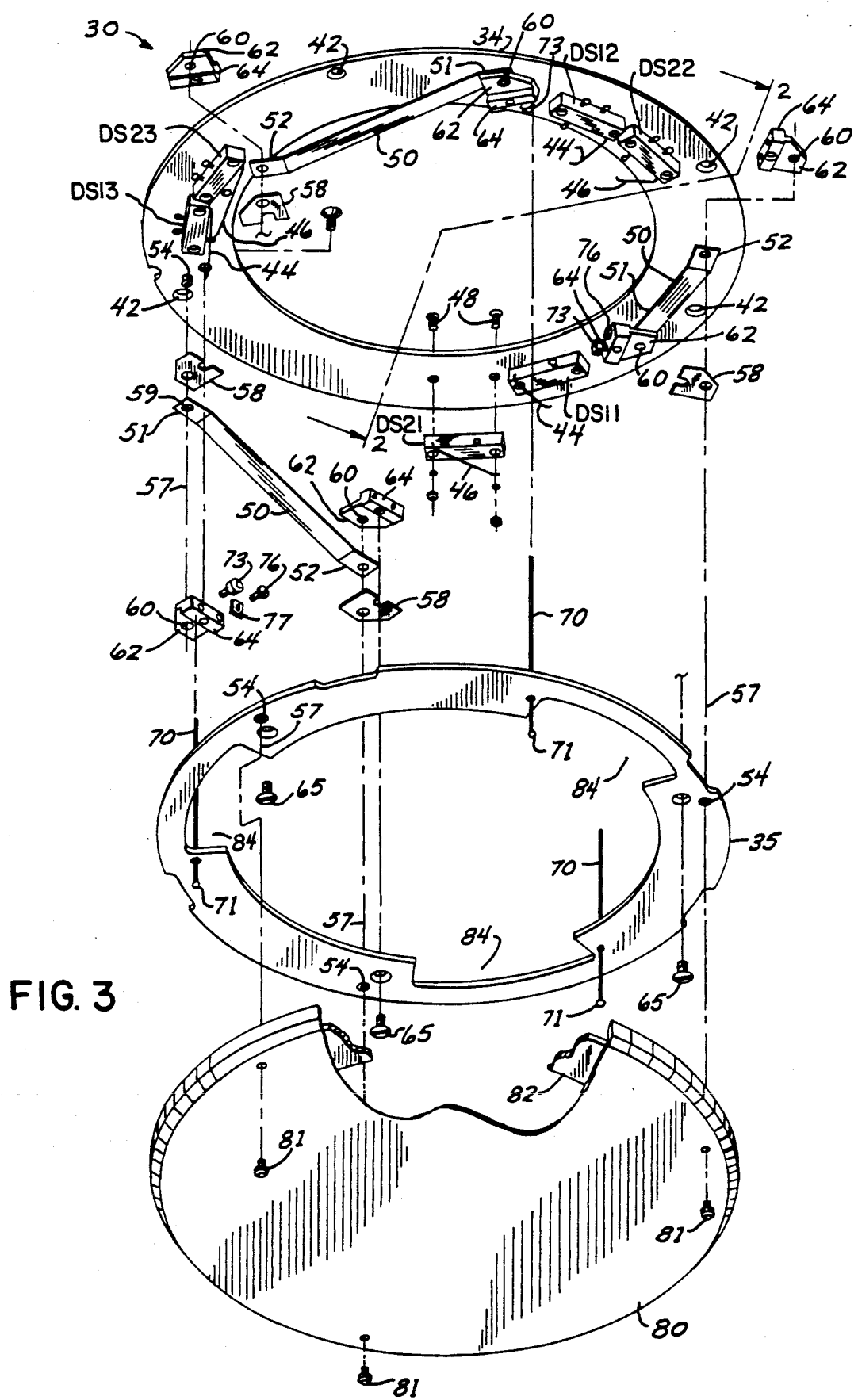
FIG. 3 is an exploded perspective view of a face collision sensor of the invention which forms a part of the collision sensor of FIG. 2.

As best shown in FIG. 3, the base plate 34 and support plate 35 are ring shaped. Each of the plates 34 and 35 has a diameter sufficient to allow x-rays to pass through it along the longitudinal axis L to the image receiver. In the preferred embodiment, each plate 34 and 35 is made of light weight metallic material, such as aluminum, and has an outside diameter of approximately 12 inches and an inside diameter of approximately 9 inches.

The base plate 34 has holes 42 for mounting the base plate 34 to the image receiver 14 with bolts or other fasteners (not shown). The base plate 34 also mounts two sets or levels of three proximity sensors each. The first level of proximity sensors is designated in the drawings as DS11, DS12 and DS13, the first numerical digit identifying the set or level of the switch and the second numerical digit identifying each switch of the level. The second level of switches is identified in the drawings as DS21, DS22 and DS23, using the same numbering code. Each of the sensors of both sets is identical, being a mechanically actuated proximity switch, except that the lever arm actuators 44 of the first set of switches DS11, DS12 and DS13 are shorter than the lever arm actuators 46 of the second set of switches DS21, DS22 and DS23. Each of the switches is mounted to the base plate 34 with appropriate fasteners 48, with the switches DS11 and DS21 in close proximity to one another, switches DS12 and DS22 in close proximity to one another and the switches DS13 and DS23 in close proximity to one another.

Flat springs 50 bias the support plate 35 and base plate 34 longitudinally apart. In the parked position of the preferred embodiment, the support ring 35 is spaced approximately 1⅛ inches away from the base plate 34 and is in a plane which is generally parallel to the plane of the base plate 34. Each spring 50 has an upper end 51 secured to the base plate 34 and extends in a counterclockwise direction from the upper end 51 to a lower end 52, which is secured to the support plate 35.

Each of the springs 50 are arranged around the perimeter of the plate 34 to extend generally in the same circumferential direction as they angle from the base plate 34 toward the support plate 35. For example, in the embodiment disclosed as viewed from the bottom such as in FIG. 4, each spring extends generally in the counterclockwise circumferential direction (i.e., either clockwise or counterclockwise) as it declines from the base plate 34 to the support plate 35. It should also be noted that the actuators 44 and 46 for the switches DS11, DS12, DS13, DS21, DS22, DS23 also extend in the same general circumferential direction as the springs 50 angle from the base plate 34 toward the support plate 35.

The springs 50 and switch actuators 44 and 46 are all made to extend in generally the same circumferential direction between the support plate 34 and 35 because as the plates 34 and 35 are compressed together, the plate 35 rotates slightly about the longitudinal axis L relative to the plate 34. This rotation is in the same direction that the springs 50 extend from the base plate 34 to the support plate 35. As the plate 35 rotates, the frictional forces on the actuators 44 and 46 tend to rotate the actuators 44 and 46 into the actuated positions of the switches DS11-13 and DS21-23, respectively.

To allow the plates 34 and 35 to be compressed together without substantial hysteresis, the springs 50 are loosely pinned at each of their ends to the plates 34 and 35. Referring to FIGS. 4, 5 and 6, the connection of each end 51 and 52 of the springs 50 to the plates 34 and 35 is the same. The connection at the upper end 51 is illustrated. A stud 54 is pressed into the plate 34 to be firmly secured relative to the plate 34. The stud 54 has a hexagonal head 55 and a cylindrical portion 56. The cylindrical portion 56 extends beyond the bottom surface of the plate 34 through a spacer 58, through a hole 59 in the upper end 51 of each spring 50 and into a hole 60 in a mount 62. The holes 59 and 60 have a diameter slightly larger than that of the cylindrical portion 56 of stud 54 so as not to bind on the portion 56. The spacer 58 is made of spring steel or other hardened material to protect the relatively soft material of the base plate 34 against scoring or other wear which may otherwise be caused by the spring 50.

The mounting deck 62 is spaced apart from the bottom surface of the base plate 34 so as to provide a clearance between the deck 62 and the spring 50. As best shown in FIG. 5, the deck 62 has a base 64 which seats against the spacer 58 and is clamped thereagainst by fastener 65, which extends through plate 34 and spacer 58. This connection clamps the spacer 58 against the plate 34 while allowing the spring 50 to rotate about axis 57 of stud 54, which axis is generally parallel to longitudinal axis L, as the plates 34 and 35 are compressed together.

The springs 50 are preferably flat springs but any type of biasing means could be used. The springs 50 are made as long as possible for the lowest stress and highest fatigue life characteristics. Flat springs are preferred of a sufficient width and height to length ratio to provide good lateral stability against the support plate 35 being shifted radially relative the base plate 34. The springs 50 should also be chosen so that a force of less than 40 pounds, and preferably less than approximately 15 pounds, applied anywhere across the area of the support plate 35 will cause a sufficient compression of the rings 34 and 35 to actuate at least one of the switches DS11-13 or DS21-23. In the preferred embodiment, at least one switch is actuated upon the application of approximately 3-5 pounds force longitudinally anywhere across this area. The springs 50 in the preferred embodiment are each approximately 5⅜ inches long, ½ inch wide and 0.032 thick, made of spring steel, and have a spring constant of approximately 1.2 pounds force per inch.

The springs 50 are prestressed in the preferred embodiment so that a force of less than approximately 5 pounds applied longitudinally to the center of the sensor 30 will not cause a sufficient compression of the plates 34 and 35 together to actuate any of the sensors DS11-13 or DS21-23. Three wire ropes 70 extend between the base plate 34 and support plate 35 in the parked position to provide the prestressing of the springs 50. The wire ropes 70 also prevent accidental extension of the support plate 35 away from the base plate 34.

The wire ropes 70 are collapsible when the plates 34 and 35 are compressed together, and non-distensible, to reliably return the support plate 35 to the parked position with minimal hysteresis. A bead 71 fixed at the lower end of each wire rope 70 is received in a depression in the lower surface of the support plate 35. The rope 70 extends from the bead 71 through the support plate 35 in a longitudinal direction to a block 73 which is screwed into the side of the base 64 of the mounting deck 62 which is secured to the base plate 34 above the bead 71. The rope 70 wraps around the block 73 for about 90° and is trapped against the base 64 by a screw 76 bearing against a washer 77 which pinches the rope 70 against the base 64. The excess free end of the wire rope can then be tucked beneath an appropriate clip 78 so as not to interfere with operation of the collision sensor 30 or extend into the x-ray path. It is preferred to have the block 73, the screw 76, the washer 77 and the sensors DS11-13 and DS21-23 mounted on the base plate 34 rather than the support plate 35 to minimize the "sprung" weight of the support plate 35, which results in lower spring stress and lower hysteresis to return the sensor 30 to the parked position.

The block 73 has an enlarged head 74 which insures positioning of the rope 70 on a reduced diameter shank 75 of the block 73. This connection of each rope 70 is preferred so that upon compression of the plates 34 and 35 together, the ropes 70 collapse in a controlled direction. While wire rope is preferred, any collapsible, non-distensible rope-like, strap-like or other suitable device could be used.

Spanning the bottom surface of the support plate 35 is a circular face plate 80, preferably made of thin plastic material which has a low attenuation to x-ray radiation. In the preferred embodiment, 0.025 inch thick polycarbonate plastic material sold under the designation Lexan TM by General Electric Company is used. A stiffener ring 82, made of ⅛ inch thick Lexan TM in the preferred embodiment, may be bonded to the face plate 80 to lend additional rigidity to the face plate 80. The studs 54 in the support plate 35 are tubular and internally threaded to receive fasteners 81 which secure the face plate 80 and stiffener ring 82 to the support plate 35.

The support plate 35 has three spaces 84 cut out from its internal diameter at the locations of actuators 44 and 46. The lower ends of the actuator 44 and 46 bear against the stiffener rings 82, rather than against the support plate 35. This is to reduce the overall thickness of the collision sensor 30 by the thickness of the support plate (approximately ⅛ inch). The co-efficient of friction between the actuators 44 and 46 and the stiffener ring 82, which is preferably a plastic material, is also lower than it would be between the actuators 44 and 46 and the support plate 35, which is preferably a metallic material such as a aluminum.

There are three switches in each level of switches equally spaced apart by 120°, three springs 50 equally spaced apart by 120°, and three ropes 70 equally spaced apart by 120°. There are three of each so that each set of elements defines a plane. Thus, the ropes 70 can be adjusted to place the support ring 35 in a plane which is parallel to the base plate 34 in the parked position. Since the springs 50 are equally spaced apart, the force required to compress the plates 34 and 35 together at any point across the face plate 80 is relatively constant. Since there are three spaced apart level one switches, no matter where the collision occurs across the face plate 80, at least one of the switches will be actuated when the required minimum actuation travel for the level one switches has been achieved. Similarly, when the required minimum actuation travel required for the level two switches has been achieved, at least one of them will be actuated no matter where across the face plate 80 the collision occurs. Note that in a collision, the face plate 80, and therefore the support plate 35, does not necessarily stay parallel to the base plate 34 but is free to become skewed relative to the base plate 34.

Figure 7:
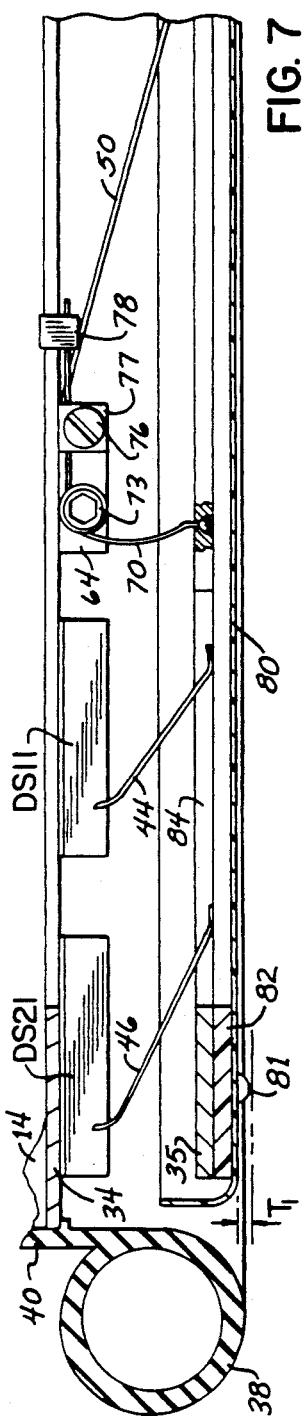
FIG. 7 is a view similar to FIG. 2 but showing the axial collision sensor partially compressed.
Figure 8:
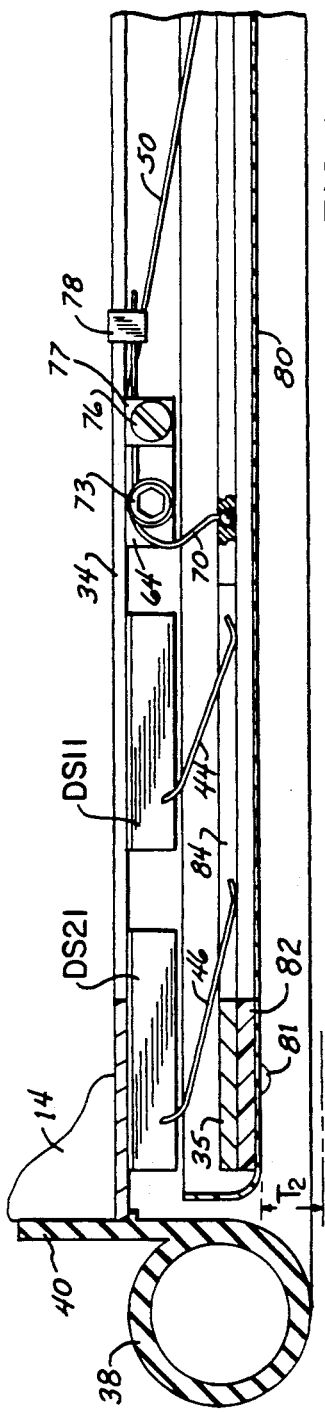
FIG. 8 is a view similar to FIG. 7 but showing the axial collision sensor further compressed.
Figure 9:
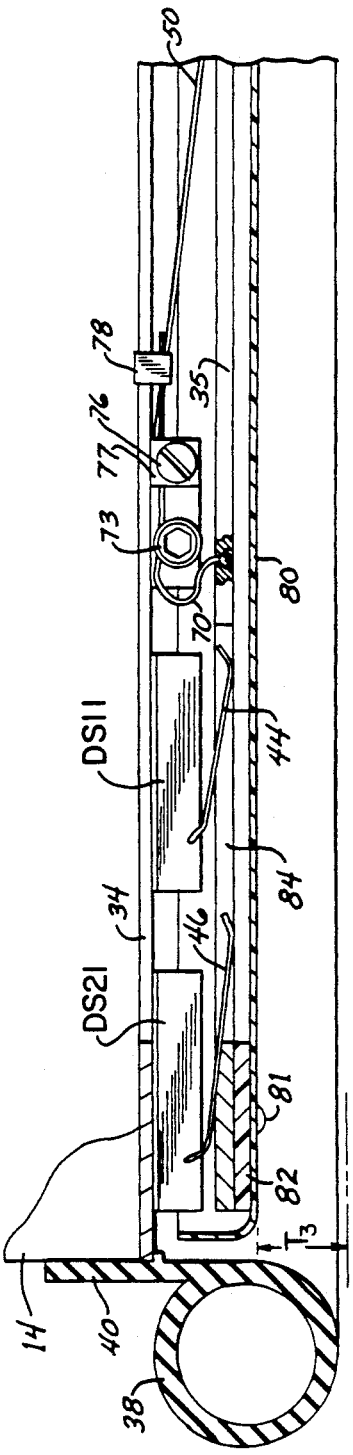
FIG. 9 is a view similar to FIGS. 7 and 8 but showing the axial collision sensor still further compressed.

FIGS. 7-9 show the action of the face collision sensor 30 through progressively increasing stages of compression. As shown in FIG. 7, when the forces produced by an object or person colliding with the face plate 80 at any point on the face plate 80 are sufficient to move at least one of the actuators 44 a first predetermined travel $T_1$ from the parked position (shown with the phantom line), one or more of the ropes 70 become slack and the first level switch DS11, DS12 and/or DS13 associated with the displaced actuator(s) 44 becomes actuated. A signal produced by one or more of the first level switches becoming actuated may be used for any appropriate purpose, such as for signalling a controller of the x-ray machine 10 to stop the motion of the machine. If the travel $T_1$ and the force required to produce that travel is relatively small, e.g., $T_1$ is 0.10 inches in the preferred embodiment and produced by a longitudinal force of approximately 5 lbs. or less applied anywhere across the faceplate 80, the machine need not be brought to a sudden halt, but can be brought to a controlled stop which initiates immediately upon actuation of one of the switches DS11-13. In this type of stop, rather than suddenly applying a brake or freezing up the machine all at once, a relatively slow braking action can be applied to stop the machine over a controlled distance.

In the preferred embodiment, the machine is controllably stopped in less than 0.30 inches, which is the required additional distance to actuate one or more of the second level switches DS21, DS22 and DS23. Thus, the travel $T_2$ shown in FIG. 8 from the parked position which is required to actuate at least one of the first level switches DS11-13 and at least one of the second level switches DS21-23 is 0.40 inches in the preferred embodiment. In the event that one or more of the second level switches is actuated, thereby signalling a malfunction, a sudden stoppage of the machine is warranted, such as by suddenly applying a mechanical or electrical brake to the machine drives. An additional travel of only 0.20 inches in the preferred embodiment is therefore allowed between the travel $T_2$ shown in FIG. 8 and the travel $T_3$ shown in FIG. 9. In the position shown in FIG. 9, at least one of the switches of both levels of switches is actuated, as in the position of FIG. 8.

Under normal circumstances, it is desirable to initiate stopping the machine when one or more of the first level switches becomes actuated, and to bring the machine to a halt before it has travelled a distance sufficient to actuate one or more of the second level switches. If this can be done, then the machine can simply be moved away from the object or person it has collided with without first implementing more complex and time consuming maintenance or check-out procedures. That way, if one or more of the second level switches is ever actuated, that can be used to signal that there has been a machine malfunction or that further inspection of the machine before continuing operation is required.

As described above, the collision sensor 12 also includes an edge sensor 32. The air bladder 38 of the edge collision sensor 32 forms a closed pressure chamber. As with the level one and level two switches of the face collision sensor 30, two levels of pressure are detected in the air bladder 38. Level one corresponds to a slight pressure increase of about 0.3 inches of water in the preferred embodiment, which would result from a minor collision with the bladder 38 as the bladder wall is initially contacted and depressed. If the bladder wall is depressed further, the pressure continues to increase, and when it is increased by about another 4.6 inches of water, a level two collision is signalled. An edge collision sensor similar to the edge collision sensor 32 has been in use on x-ray imaging apparatus commercially designated LP TM by General Electric Company.

Figure 10:
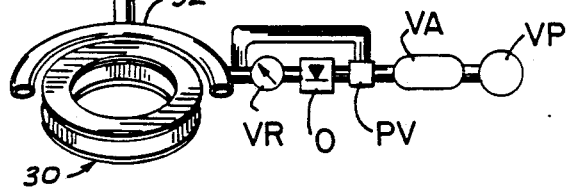
FIG. 10 is a schematic pneumatic circuit diagram for a collision sensor of the invention.

By way of brief description of the edge collision detection system, FIG. 10 illustrates tubing 85 connecting air bladder 38 to a first level pressure sensor switch PS1 and to a second level pressure sensor switch PS2. The leak tightness of the air bladder 38, the sensors PS1 and PS2 and the tubing 85 is monitored continuously as a fail-safe measure. This is done by applying a slight vacuum reference level of approximately 5.1 inches of water to the system. Any leaks would admit air into the system and reduce the vacuum level, which will actuate PS1 and/or PS2. Preferably, PS1 also provides a high system vacuum level switch point so that it becomes actuated if the vacuum in the bladder exceeds a certain level. The upper level at which the switch PS1 becomes actuated in the preferred embodiment is 5.8 inches of water. Therefore, if the vacuum in the air bladder 38 is less than or equal to 4.8 inches of water or is greater than or equal to 5.8 inches of water, the switch PS1 will be actuated.

Any suitable vacuum supply system may be used to provide the vacuum reference level to the air bladder 38, and in the preferred system, a high vacuum of 14 to 20 inches of mercury is provided by a two liter vacuum accumulator VA that is provided by a vacuum pump VP. The high vacuum is reduced to the reference level of the air bladder 38 by a vacuum regulator VR. A small diameter restriction O is used to slow the speed at which vacuum level correction can occur. Serious leaks cannot be compensated and causes the vacuum level to decrease and the switches PS1 and/or PS2 to be actuated. Also, preferably, a pressure operated valve PV is provided in the supply which closes off the line from the accumulator VA to the air bladder 38 when the air bladder vacuum drops to less than 4.8 inches of water. In this way, the collision pressure is maintained until the collision is cleared. Otherwise, the vacuum regulator would return the system pressure to 5.1 inches of water and the collision signal would be lost. This valve, however, must be held open, such as by a solenoid operated electrical override, to initially establish the 5.1 inch water vacuum in the air bladder, such as during powering up of the x-ray apparatus 10.

Figure 11:
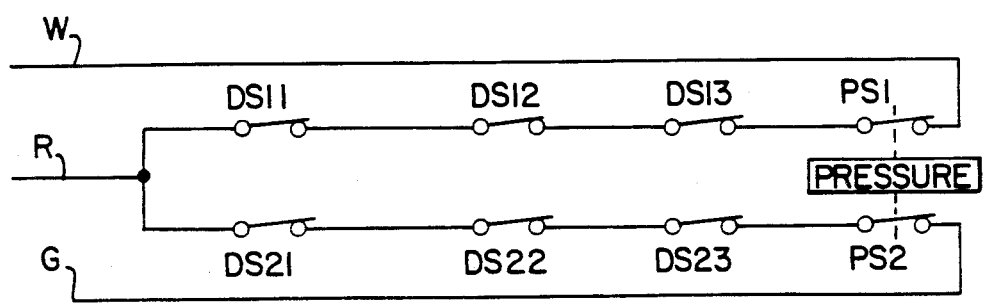
FIG. 11 is a schematic electrical circuit diagram for a collision sensor of the invention.

FIG. 11 illustrates an electrical schematic for the collision sensor 12. All of the first level switches, including the proximity sensors DS11, DS12 and DS13, as well as the pressure sensor PS1, are electrically connected in series. Similarly, all of the second level proximity sensors DS21, DS22 and DS23, and the second level pressure sensor PS2, are electrically connected in series. Thus, a voltage or current provided at conductor R will be carried through to conductor W if none of the first level sensors are actuated. However, if any or all of the sensors DS11, DS12, DS13 and PS1 are actuated, the reference voltage applied to conductor R will be interrupted as detected at conductor W. Similarly, the reference voltage applied to conductor R will be carried through to conductor G only if all of the second level sensors DS21, DS22, DS23 and PS2 are not actuated. Upon actuation of one or more of the second level sensors, the reference voltage will be interrupted at conductor G, thereby signalling a second level collision.

We claim:

1. A collision sensor, comprising:
   a base plate defining a base plane and a longitudinal axis perpendicular to said plane;
   a support plate spaced apart from said base plate along said longitudinal axis and defining a support plane;
   means for biasing said support plate away from said base plate along said longitudinal axis;
   collapsible, non-distensible extension limiting means extending between the base plate and the support plate in a direction generally parallel to said longitudinal axis for positioning said support plane parallel to said base plane when said means are fully extended; and
   means positioned between said base and support plates for sensing the proximity of said support plate to said base plate.

2. A collision sensor as in claim 1, wherein said base and support plates are ring shaped, defining a radiation transmission path therethrough along the longitudinal axis.

3. A collision sensor as in claim 2, further comprising a face plate fixed to a side of said base plate and covering said radiation transmission path, said face plate being made of a low attenuation material which is substantially transparent to said radiation.

4. A collision sensor as in claim 1, wherein the extension limiting means comprises three rope-like lines connecting the base plate to the support plate at spaced apart angular locations about said longitudinal axis.

5. A collision sensor as in claim 4, further comprising means for securing each said line to the base plate, a block on the base plate, and means for securing each said line to the support plate, wherein each said line extends from the base plate securing means to the block, partially around the block, and from the block toward the support plate to the support plate securing means.

6. A collision sensor as in claim 1, wherein the biasing means comprises at least one flat spring extending between the base plate and the support plate.

7. A collision sensor as in claim 6, wherein three of said flat springs extend between the base plate and the support plate at locations which are equally spaced apart angularly about said longitudinal axis.

8. A collision sensor as in claim 7, wherein each of said flat springs angles from said base plate to said support plate in generally the same circumferential direction.

9. A collision sensor as in claim 8, wherein the sensing means comprises at least one mechanically actuated switch, said switch having a rotary actuator arm angling from the base plate to the support plate in generally the same circumferential direction that the flat springs extend from the base plate to the support plate.

10. A collision sensor as in claim 6, wherein each said flat spring has one end adjacent to the base plate and an opposite end adjacent to the support plate, and further comprising means for securing each said end to said adjacent plate, said securing means allowing said spring to rotate slightly about an axis parallel to the longitudinal axis when the base and support plates are compressed together.

11. A collision sensor as in claim 10, wherein the securing means provides a loosely pinned connection between each said end of each spring and the plate adjacent to said end.

12. A collision sensor as in claim 1, wherein the sensing means comprises a first set of at least three switches fixed to the base plate and angularly spaced approximately 120° apart about said longitudinal axis, each said switch having an actuator arm extending toward the support plane for actuation when the longitudinal spacing between the support plane and the base plane at the position of said switch has been reduced by a first predetermined travel.

13. A collision sensor as in claim 12, wherein the sensing means further comprises a second set of at least three switches fixed to the base plate and angularly spaced approximately 120° apart about said longitudinal axis, said switches of said second set each having an actuator arm extending toward the support plane for actuation when the longitudinal spacing between the support plane and the base plane at the position of said switch has been reduced by a second predetermined travel which is greater than said first predetermined travel.

14. A collision sensor as in claim 13, wherein the collision sensor is mounted to a power driven member of a machine, and the difference between the first predetermined travel and the second predetermined travel is greater than the overtravel of the member which the member goes through after at least one of the first set of switches is actuated.

15. A collision sensor as in claim 1, further comprising a pressure sensitive bladder surrounding the support plate and means connected to said bladder for sensing changes in pressure in the bladder.

16. A collision sensor, comprising:
   axial displacement sensitive means responsive to a collision along an axial direction, said means including at least one switch which is actuated when the displacement of said means exceeds a certain predetermined travel;
   a closed deformable bladder separate from and surrounding said axial displacement sensitive means, said bladder containing a fluid of a predetermined pressure and producing a change in the pressure of said fluid upon deformation of said bladder in a radial direction; and
   a pressure sensitive switch separate from said displacement sensitive switch for sensing pressure changes in said bladder.

17. A collision sensor as in claim 16, wherein said axial displacement sensitive means includes two plates, means for biasing said plates apart axially and wherein said displacement sensitive switch is between said plates.

18. A collision sensor, comprising:
   a base plate defining a base plane and a longitudinal axis perpendicular to said base plane;
   a support plate spaced apart from said base plate along said longitudinal axis and defining a support plane;
   means for biasing said support plate away from said base plate along said longitudinal axis;
   collapsible, non-distensible extension limiting means extending between the base plate and the support plate along said longitudinal axis, said means positioning said support plane in a parked position parallel to said base plane when said means are fully extended;
   means positioned between said base and support plates for sensing the proximity of said support plate to said base plate;
   said base and support plates being annular to define a radiation transmission path therethrough which is parallel to said longitudinal axis; and
   said extension limiting means comprising three rope-like lines connecting the base plate to the support plate at spaced apart angular locations about said longitudinal axis.

19. A collision sensor as in claim 18, wherein the biasing means comprises at least one flat spring extending between the base plate and the support plate.

20. A collision sensor as in claim 19, wherein the sensing means comprises a first set of at least three switches fixed to the base plate and angularly spaced approximately 120° apart about said longitudinal axis, each said switch having an actuator arm extending toward the support plane for actuation when the longitudinal spacing between the support plane and the base plane at the position of said switch has been reduced by a first predetermined travel.

21. A collision sensor as in claim 20, further comprising a pressure sensitive bladder surrounding the support plate and means connected to said bladder for sensing changes in pressure in the bladder.

* * * * *